US008782087B2

(12) United States Patent
Sengupta et al.

(10) Patent No.: US 8,782,087 B2
(45) Date of Patent: Jul. 15, 2014

(54) ANALYZING LARGE DATA SETS TO FIND DEVIATION PATTERNS

(75) Inventors: Arijit Sengupta, San Mateo, CA (US); Brad A. Stronger, San Mateo, CA (US); Daniel Kane, Menlo Park, CA (US)

(73) Assignee: BeyondCore, Inc., San Mateo, CA (US)

( * ) Notice: Subject to any disclaimer, the term of this patent is extended or adjusted under 35 U.S.C. 154(b) by 0 days.

(21) Appl. No.: 13/249,168

(22) Filed: Sep. 29, 2011

(65) Prior Publication Data
US 2012/0053959 A1    Mar. 1, 2012

Related U.S. Application Data

(63) Continuation-in-part of application No. 12/944,554, filed on Nov. 11, 2010, now abandoned, which is a continuation of application No. 12/787,342, filed on May 25, 2010, now Pat. No. 7,849,062, which is a continuation-in-part of application No. 11/389,612, filed on Mar. 24, 2006, now Pat. No. 7,844,641, which is a continuation-in-part of application No. 11/084,759, filed on Mar. 18, 2005, now Pat. No. 7,720,822, application No. 13/249,168, which is a continuation-in-part of application No. PCT/US2011/037956, filed on May 25, 2011.

(51) Int. Cl.
*G06F 17/30* (2006.01)
(52) U.S. Cl.
CPC ........................................ *G06F 17/30* (2013.01)
USPC ............ 707/791; 707/802; 707/822; 707/600

(58) Field of Classification Search
USPC .................................................. 707/600–899
See application file for complete search history.

(56) References Cited

U.S. PATENT DOCUMENTS

| | | | |
|---|---|---|---|
| 5,251,131 | A | 10/1993 | Masand et al. |
| 5,488,725 | A | 1/1996 | Turtle et al. |
| 7,720,822 | B1 | 5/2010 | Sengupta |
| 7,844,641 | B1 | 11/2010 | Sengupta et al. |
| 7,849,062 | B1 | 12/2010 | Sengupta et al. |
| 7,925,638 | B2 | 4/2011 | Sengupta et al. |
| 7,933,878 | B2 | 4/2011 | Sengupta |
| 7,933,934 | B2 | 4/2011 | Sengupta |
| 8,019,734 | B2 | 9/2011 | Sengupta |
| 2004/0133531 | A1* | 7/2004 | Chen et al. .......................... 706/8 |
| 2006/0089924 | A1 | 4/2006 | Raskutti et al. |
| 2008/0010274 | A1 | 1/2008 | Carus et al. |
| 2008/0267505 | A1 | 10/2008 | Dabet et al. |
| 2011/0055620 | A1 | 3/2011 | Sengupta |

FOREIGN PATENT DOCUMENTS

WO   WO 2011/149608 A1   12/2011
WO   WO 2011/150097 A2   12/2011

OTHER PUBLICATIONS

PCT International Search Report and Written Opinion, PCT Application No. PCT/US11/37956, Nov. 9, 2011, 15 pages.
U.S. Appl. No. 11/904,850, filed Sep. 28, 2007, Arijit Sengupta.

\* cited by examiner

*Primary Examiner* — Isaac M Woo
(74) *Attorney, Agent, or Firm* — Fenwick & West LLP

(57) ABSTRACT

Operations, such as data processing operations, can be improved by applying clustering and statistical techniques to observed behaviors in the data processing operations.

19 Claims, 5 Drawing Sheets

ANALYZING LARGE DATA SETS TO FIND DEVIATION PATTERNS

CROSS REFERENCE TO RELATED APPLICATIONS

This application is a continuation-in-part of U.S. patent application Ser. No. 12/944,554 filed Nov. 11, 2010; which is a continuation of U.S. Pat. No. 7,849,062 filed May 25, 2010; which is a continuation-in-part of U.S. Pat. No. 7,844,641 filed Mar. 24, 2006; which is a continuation-in-part of U.S. Pat. No. 7,720,822 filed Mar. 18, 2005. This application is also a continuation-in-part of PCT/US11/37956, filed May 25, 2011. All of the foregoing are incorporated by reference in their entirety.

BACKGROUND

The present invention relates generally to quality management in a data-processing environment. Specifically, it relates to operational risk estimation and control associated with a data processing operation.

Errors in documents during a data processing operation, for example, data entry and data transformation are common. These errors may result in significant losses to an organization, especially if a large amount of data is processed. It is therefore important to control the quality of documents. Conventional techniques for controlling the quality of documents include error detection and correction, and determination of parameters for measuring errors. One such measurement parameter can be the percentage of documents with errors. However, these parameters do not directly indicate the impact of the errors to the organization.

Further, the conventional techniques for error detection are manual in nature. Errors can be detected by manually checking a set of documents to catch errors and compute the error rate. However, this technique may be error prone since the errors are detected manually. Further, the number of documents to be reviewed for catching errors (rather than just estimating error rates) is a function of the error rate. If the error rate is high, then a high percentage of documents need to be reviewed for catching a higher percentage of errors. Consequently, this technique can be labor intensive and therefore expensive.

Another technique for error prevention involves double typing the same document. The two different versions of the same document are compared electronically, and any discrepancies are reviewed and corrected. However, in this case each document needs to be double typed, which can be a labor-intensive exercise. The double typing and the confirmation of its correctness are done on a larger set of the documents. Further, a supervisor has to manually review each discrepancy to detect which of the two operators has made an error, or to correct the errors. Further, manual reviews themselves are prone to errors and result in wastage of labor, money and time. Conventional techniques for detection of errors and correction are therefore cumbersome and expensive.

Furthermore, data entry operators can become aware as to when the supervisors are carrying out quality checks, and concentrate on quality for that period. If the process requires double entry of a complete document, it may result in 'gaming' of the system by the data entry operators, i.e., they may be lax in the initial data entry and catch errors if there is a discrepancy.

In other conventional techniques, critical fields are predefined by a supervisor/management. These critical fields are defined on the basis of their subjective criticality. Subsequently, preventive and corrective measures are taken in these critical fields. Further these critical fields themselves are not updated automatically and are only updated periodically during management review. As a result, the quality of the processed document may not be improved beyond a certain extent.

Accordingly, there is a need for developing techniques that manage the quality of documents. Such techniques should be cost-effective, scalable, and less time-consuming. There is a need for techniques that can measure error rate, control error rate, predict errors, and enable their subsequent prevention. Further, there is a need for techniques that ensure that the critical fields are identified dynamically and automatically.

Further, these techniques should enable benchmarking of organizations, i.e., how well organizations control data processing operational risk relative to one another. Such a benchmark should be comparable across process variations, organization size, document type, etc. Also, measurement schemes for data processing operators and systems should be directly correlated to measures used to evaluate the organizations. This enables true alignment of measurement schemes with performance requirements. These techniques should also deter 'gaming' of the system by data entry operators and supervisors.

SUMMARY

Various embodiments of the invention provide methods and systems for identifying critical fields in documents, for example so that quality improvement efforts can be prioritized on the critical fields.

One aspect of the invention concerns a method for improving quality of a data processing operation in a plurality of documents. A set of documents is sampled. An error rate for fields in the documents is estimated based on the sampling. Critical fields are identified based on which fields have error rates higher than a threshold. Which fields are the critical fields may be automatically updated on a dynamic basis. In one approach, the error rate for a field is based on both a frequency of errors in the field and a relative weight for that field. For example, the relative weight might be based on the operational impact of data processing errors in that field.

Various types of thresholds can be used. For example, the threshold may be a predetermined constant value. Alternately, the threshold may vary as a function of the relative weight of a field. It may also be adjustable, either by the user or dynamically based on the sampled documents. The threshold may be an aggregate across multiple fields, not just a threshold for a single field. For example, the set of critical fields may be determined by selecting the critical fields with the highest error rates until the aggregate sum of error rates reaches a threshold. The threshold can also vary as a function of the distribution of error rates for the fields. For example, if the distribution of error rates is bimodal, the threshold may be set at some point between the two modes.

In various embodiments, the error rate for a field is determined in part by estimating a probability that data entered for a field in a document is in error, without knowing a correct transcription for the field. The data entered for a given field typically has a distribution among the different answers provided. Data-entered answers that are identical form a cluster. For example, if three operators type (or otherwise data enter) the same answer for a field, that is a cluster. A mode is the cluster for the most frequently appearing answer. There can be multiple modes if different answers are data-entered with the same frequency.

In one aspect, estimating the probability of error accounts for clusters, modes and/or their equivalencies. Equivalencies can be determined based on the number of and sizes of clusters, as well as other factors. In one approach, the clusters that have the largest size for a field are determined to be equivalent and correct answers. In another approach, these clusters are determined to be not equivalent. Nevertheless, a single cluster is not selected as the correct answer. Rather, each non-equivalent cluster is assigned a probability of being a correct answer that is a function of the cluster's size. In yet another approach, the cluster, for which the associated operators have a lower average historical error rate, is selected as a correct answer for a field. Clusters could also be selected as the correct answer, based on whether the associated operators have a lower error rate for the field within the set of documents currently being evaluated or whether the associated operators have a lower historic error rate for the field. Estimating the correct answer can also take into account whether the data entered for a field is the default value for that field.

Various embodiments of the present invention further provide methods and systems for quality management of a plurality of documents for a data-processing operation in an entity. Each document comprises at least one field. The entity includes an organization, or one or more employees of the organization.

In an embodiment of the invention, the method measures the quality of a plurality of documents in a data-processing operation. A relative operational risk is assigned for errors in each field of the plurality of documents. The assignment is based on the relative operational impact of the errors, and a frequency of errors is determined for each field. Finally, an error rate is determined, based on the relative operational risk and the frequency of errors associated with each field.

In another embodiment, a method for quality management of a plurality of documents for a data-processing operation in an entity is provided. The method comprises determination of error rates. Further, critical fields in the documents are dynamically identified based on the relative operational impact and the frequency of errors in the various fields. Errors are then reduced in the critical fields by using, for example, double typing of the data in the critical fields.

Further, the occurrence of errors is predicted by determining a correlation between them and a set of process and external attributes. The possibility of occurrence of the errors is notified to a supervisor if the attributes exhibit the characteristics correlated with errors. The supervisor can then take preventive measures. Alternatively, other preventative/corrective actions can be taken based on the predictions. This process of error prediction, error rate computation and error prevention can be performed independently or iteratively, thereby reducing the occurrence of the errors. Further, the set of error correlation attributes and the set of critical fields also get updated depending upon changes in the measured error rate.

In an embodiment of the invention, a set of documents is randomly identified for the purpose of sampling. Such a random sampling is used for determining the probability of errors related to specific fields of the documents.

In another embodiment of the invention, the 'operational risk weighted error' is identified for each employee for each field corresponding to the randomly sampled documents. This helps in identifying the specific training needs of the employees and in better targeting training efforts. Employees may also be assigned to various tasks based on their error rates.

Furthermore, a pattern of errors can be identified at a process level and an employee level. The identified error patterns are then correlated with the root causes of errors. Subsequently, on the basis of the correlation, a database is generated. The database can then be used for identifying the root causes of further error patterns. The database can be used to diagnose the root cause of an error pattern, for example, the root cause of an error pattern can be training related or process related or system related. Once an error pattern (or high frequency of errors) corresponding to a field has been identified, either for individual employees or for groups of employees, the database can also be used for a predictive diagnosis of the error. The diagnosis may be a training, system or process error. If the diagnosis identifies a training need, then the method described in the previous paragraph can be used to better allocate training resources to the specific weaknesses of the employee or to specific weak employees. Employees may also be assigned to various tasks based on their error patterns.

Furthermore, the database can provide information regarding the historic diagnosis of previously observed error patterns corresponding to a field and/or an employee. For example, the database can provide historic data about diagnosis of a previous error or error pattern, and the methodology adopted at that time for mitigating the error.

The quality management system pertaining to the plurality of documents includes means for determining error rates. The means for reducing errors is responsible for reducing errors by focusing on critical fields in the plurality of documents. It also updates the critical fields based on changes in error rates and patterns. The means for predicting the occurrence of errors predicts errors by determining a correlation between the errors and a set of attributes. It also updates the set of attributes based on changes in error rates and patterns. A means for controlling is used to coordinate between the remaining system elements of the quality management system. The means for controlling keeps a tab on the quality of the plurality of documents.

Other aspects of the invention include components and applications for the approaches described above, as well as systems and methods for their implementation.

BRIEF DESCRIPTION OF THE DRAWINGS

The preferred embodiments of the invention will hereinafter be described in conjunction with the appended drawings provided to illustrate and not to limit the invention, wherein like designations denote like elements, and in which.

DESCRIPTION OF PREFERRED EMBODIMENTS

Various embodiments of the present invention relate to quality management of an entity for a data-processing operation and provide methods and systems pertaining to operational risk control in the data-processing operations. Data processing operations include, but are not limited to, data entry, transfer, storage, reporting and transformation. The entity can be an organization such as a business process outsourcing organization or an in-house corporate data processing operation. The entity can also be one or more employees of the organization. Various embodiments of the invention measure error rate associated with a data processing operation for an employee or an organization. This involves identifying the relative operational impact associated with the errors and the frequency of the errors. Further, critical fields, i.e., the fields wherein the product of the relative operational impact of errors and error frequency can be large are identified.

In an embodiment of the invention, critical fields are identified based on the frequency of errors and the relative operational impact of the errors in the fields. Data in these critical fields can be double typed to ensure that the errors in these critical fields are reduced. Subsequently, these critical fields can be updated and the process repeated on the new identified critical fields.

In another embodiment of the invention, occurrences of errors are also predicted based on the correlation of errors with a set of attributes. Where a high correlation is identified between occurrence of errors and an attribute, a supervisor can be alerted regarding the same. Subsequently, the supervisor can take preventive actions to avoid the occurrence of the errors. In an alternate embodiment, other corrective/preventative measures can be undertaken. The working of the error prediction process is verified by measuring the error rate. The set of attributes is then updated based on the error rate.

Figure 1:
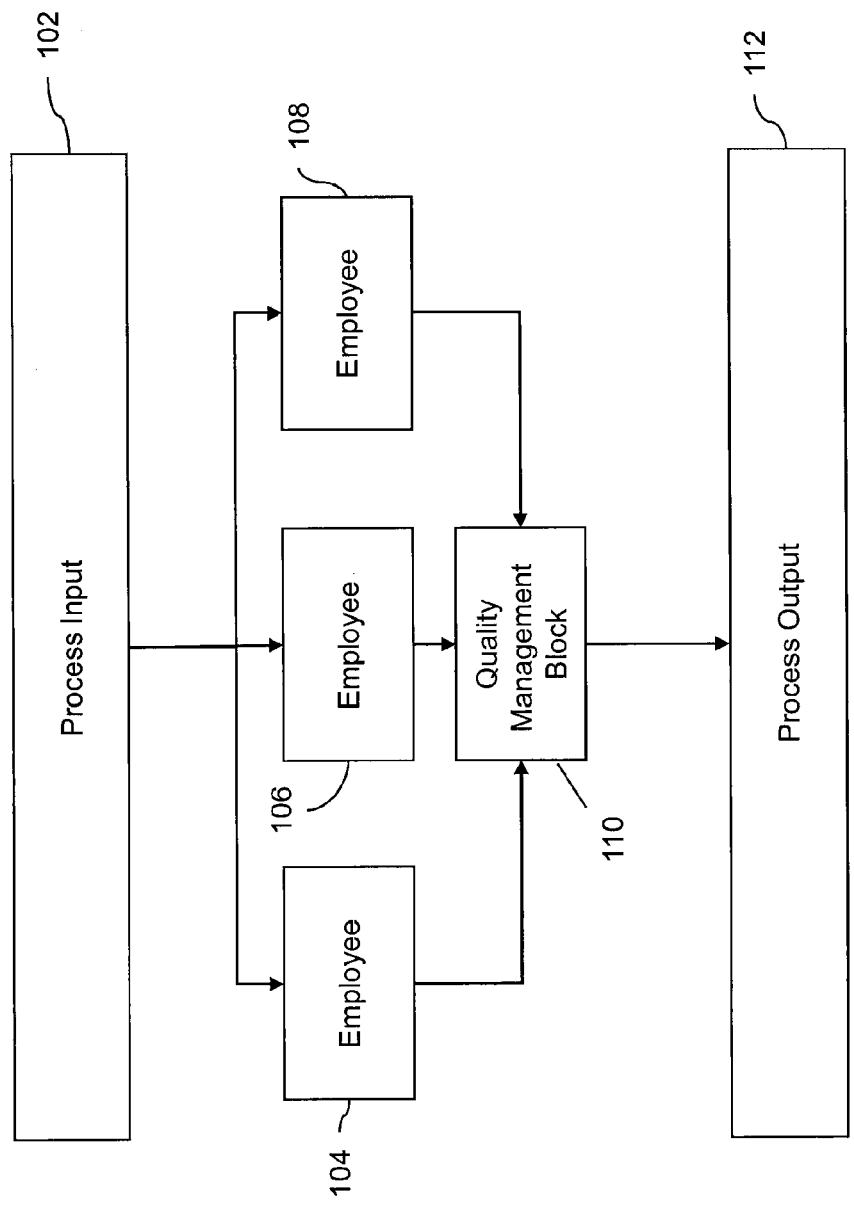
FIG. 1 is a block diagram illustrating an exemplary data-processing environment, suitable for use with the present invention.

FIG. 1 is a block diagram illustrating an exemplary data-processing environment that is suitable for use with various embodiments of the present invention. The data-processing environment includes a process input block 102 that provides the input data, which is to be processed in the form of transcribed files or documents. This input data is provided to employees 104, 106, and 108 in an organization. The employee can then process the data, for example type in the data into electronic form. Employees 104, 106, and 108 may be for example, medical transcription clerks, and data may be provided to them for medical transcription. For the sake of simplicity, only a few employees have been shown in FIG. 1. In actuality, the number of employees may be much higher. In an exemplary embodiment of the present invention, the organization is a business process outsourcing (BPO) organization. While entering data, the employee may make errors. A quality management block 110 controls the occurrence of errors in the document being processed. In general, quality management block 110 is responsible for detecting, preventing, predicting and controlling errors. The processed documents are finally sent to a process output block 112 for delivery.

Figure 2:
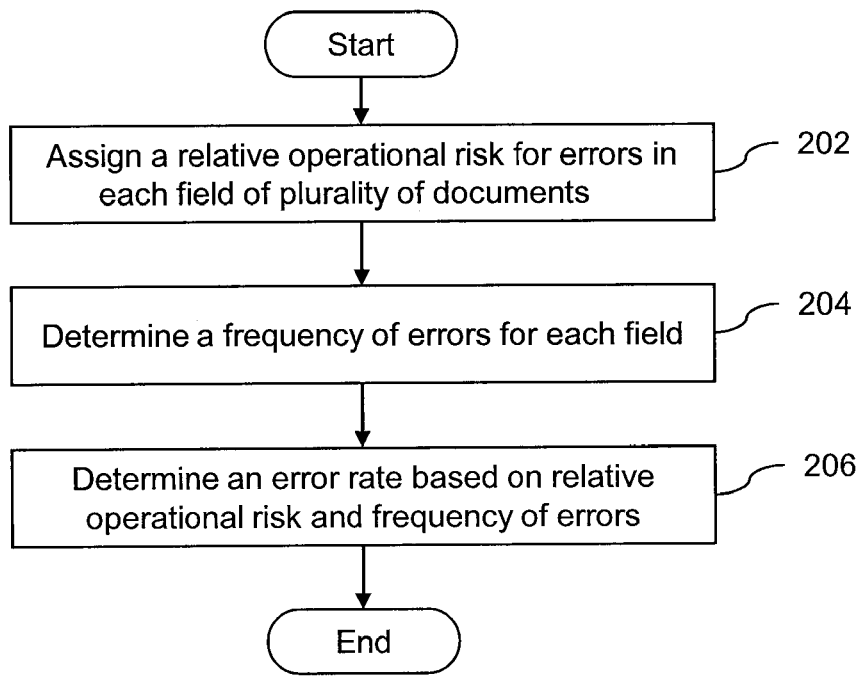
FIG. 2 is a flowchart depicting a method for measuring the quality of a plurality of documents in the data-processing environment, in accordance with an embodiment of the present invention.

FIG. 2 is a flowchart depicting a method for measuring the quality of a plurality of documents for a data-processing operation, in accordance with an embodiment of the present invention. For the purpose of illustration, the method is hereinafter described assuming a data entry operation.

Each document can include several fields. An exemplary document can include several fields such as 'Name', 'Address', 'Telephone Number', 'Email Address', 'Social Security Number', and so on. To process the document, an employee, for example a data entry operator, can enter data in each of these fields. Depending on the purpose for which the document is being processed, some fields may be more important than others, for example, the social security number can be more important than the telephone number. Therefore, an error made while entering the social security number can have a greater impact or 'operational impact' than one made while entering the telephone number. In general, each field of a document can have a different operational impact.

To measure the quality of the documents, a relative weight or 'relative operational risk' (w) is assigned to errors corresponding to each field of the plurality of documents at step 202. Operational risk refers to the risk of losses due to errors in data processing operations. Relative operational risk implies relative loss incurred due to errors in a field. The assignment is based on the operational impact of the errors, i.e., an error with a larger operational impact is weighted relatively higher than an error that has a smaller operational impact.

At step 204, a frequency (n) of errors is determined for each field in the plurality of documents, i.e., the number of errors in each field is determined. In an embodiment of the invention, n is determined by sampling a set of documents and measuring the number of errors in each field. Exemplary methods to determine n are described in the later part of the description section.

At step 206, an error rate (E) is determined. The error rate E is a measure of how well the operational risk is being controlled. E is a measure of the quality of the plurality of documents and indicates the level of operational risk attributable to the data processing activities of an employee, a group of employees or the organization. The determination of E is based on the values of w and n for a set of fields represented by $S=\{F_1, F_2, \ldots, F_i, \ldots\}$ in the plurality of documents, for example, wherein the relative operational risk of a field $F_i$ is $w_i$ and the frequency of errors is $n_i$. Therefore, the relative error rate ($e_i$) for the field $F_i$ is given as $$e_i = \frac{w_i n_i}{\sum_i w_i} \quad (1)$$

where n is equal to zero or one for a given observation. In general, the error rate for a document across all the fields in the set S is given as $$e_j = \frac{\sum_i w_i n_i}{\sum_i w_i} \quad (2)$$

where n is equal to zero or one for a given observation. The average error rate for a sample of documents is given as $$e_{avg} = \frac{\sum_{j=1}^{N} e_j}{N} \quad (3)$$

i.e., $$e_{avg} = \frac{\sum_{j=1}^{N} w_j n_j}{N \sum_{j=1}^{N} w_j}$$

where N is the number of documents in the sample. The average error rate can be normalized to a base of 100 to get the error rate E. Therefore, E=100 implies that each field in each of the documents has errors.

E can be reduced by decreasing the frequency of errors in fields with a larger operational impact. Further, E is independent of parameters such as the structure and size of documents, the total operational impact of errors in the plurality of documents, and the size of the organization. The value of E can be used to determine an expected operational risk (EOR). EOR is the operational risk that is expected from a data processing operation. In an embodiment of the present invention, the EOR is obtained by multiplying $e_{avg}$ with the operational impact of making an error in every field in each of the plurality of documents.

EOR is a measure that can be used in accounting risk reserves and is relevant for regulations such as Sarbanes Oxley and Basel II. Consequently, E is directly related to how the organization as a whole is measured, thus effectively aligning measurement and performance across the layers of the organization.

Frequencies of errors in various fields are measured by sampling a set of documents from amongst the plurality of documents. Exemplary methods to sample the documents and identify the frequency of errors in the sampled documents are hereinafter described.

In one embodiment of the present invention, a set of documents of which the correct transcriptions (entries) are known a priori, is sampled to estimate error rates. To estimate quality, a statistically significant sample size (greater than 30) is considered. The 95% confidence interval for the estimated error rate is sample mean±2× standard error of mean. It is to be noted that the sample size does not directly depend on the population size or the expected quality. However, the confidence interval could be tighter if the sample standard deviation is smaller. In an embodiment of the present invention, one or more employees type the set of documents for which transcriptions already exist. This generates a new transcribed version of each document from the set of documents. Each new transcription is then electronically compared with its corresponding known transcription, and any discrepancy between the two transcriptions is termed as an error, unless it has already been specified or learned (e.g., from cluster analysis). For example, if it is specified or learned that 'Lane' may also be typed as 'Ln.', this discrepancy is not considered to be an error. By identifying the number of such errors, n is recorded for each field in the plurality of documents. The recorded values of n are then used to determine E. In this embodiment, the E of a data entry operator is an absolute value, i.e., it is not relative to the error rates of other data entry operators.

In an alternate embodiment of the present invention, a set of sections is identified in each document from amongst the set of documents for which transcriptions already exist. A section may or may not include one or more fields. Sections from amongst the set of sections are randomly combined to generate a new set of documents, wherein correct transcriptions are known for each component section. The combination process is automated and ensures that each document in the new set of generated documents includes only one instance of each field in the original documents. In this way, a large number of documents with known transcriptions can be generated from a small number of documents with known transcriptions. For example, if there are m documents in the set of documents, and p sections in each document from amongst the set of documents, $m^p$ documents can be generated for sampling. The new set of generated documents is then provided to employees for typing. Each section of each new transcription is electronically compared with the corresponding section in the original set of documents with known transcriptions, and any discrepancy between the two transcriptions is termed as an error. As in the previous embodiment, in this embodiment the E of a data entry operator is an absolute value, i.e., it is not relative to the error rates of other data entry operators.

In another embodiment of the present invention, a set of documents is identified randomly from amongst the plurality of documents for the purpose of sampling. For each document in the sample, employees such as data processing operators are paired randomly, to generate a set of (one or more) random pairs of data entry operators. The random pairs are generated such that no employee is in more than one pair for a given document. A document from amongst the set of documents is typed by each data entry operator belonging to a pair from amongst the corresponding set of random pairs of data entry operators. In this way, each document from amongst the set of documents is typed, so that there are at least two versions of each document. The two versions are electronically compared with each other, and any discrepancy is termed as an error. The n is recorded for each field in the plurality of documents. The recorded values of n are then used to determine E. It is to be noted that the E of a data entry operator is relative to the error rates of other data entry operators. This is because a discrepancy could have been caused by either of the data processing operator in the random pair. However, the error rates of multiple random samples are considered for computing the E of the data entry operator. In an embodiment of the invention, the sample can be large enough. As a result, the random pairings of employees can be statistically 'backed out', i.e., average relative error rate of a specific employee can be measured. Moreover, the average relative frequency of errors for each field can also be accurately measured. This can be achieved without identifying the data entry operator or operators who have actually made the errors corresponding to the discrepancies. This embodiment eliminates the need for sample documents with correctly known transcriptions. This embodiment is completely automatic and can be reliably carried out in a manner where employees cannot become aware of which documents are being used for sampling and therefore cannot 'game' the sampling.

In another embodiment of the present invention, a set of documents is identified randomly from the plurality of documents for the purpose of sampling. For each document, employees such as data-processing operators are grouped randomly to generate one or more random groups of data-entry operators. Each group includes at least three data-entry operators. The random groups are so generated that no data-entry operator belongs to more than one group for a document. Each data entry operator in a group types the same document from the set of given documents. In this way, each document from amongst the set of documents is typed, so that there are at least three versions of each document. These different versions of the same document are electronically compared with each other. For each field in the document, the most common answer is identified, based on the comparison. For each field, the most common answer, hereinafter referred to as the 'plurality vote' answer, is likely to be the correct answer as there are multiple ways to get an answer wrong, but only one way to get an answer right.

While identifying the plurality vote answer, 'specified equivalencies' or 'learned equivalencies' are also considered. For example, if it is specified that 'Lane' may also be typed as 'Ln.', both versions would be considered identical for the purposes of identifying the plurality vote answer. In some cases, more than one answer may appear equally often. If there are m different answers each occurring the same number of times, and no other answer occurring more frequently, referred to as multiple modes, each of these answers have equal probability of being the correct answer. The answers are assigned the probability of (m−1)/m of being an incorrect answer. Moreover, while assigning the probability of an incorrect answer, consideration can be taken of whether a multiple mode was the default value. For example, if the data-entry screen for a "Marriage Status" field has a default value of "married," and three data entry operators selected "single," while three operators selected "married", then "single" may be selected as a 'plurality vote' answer. This is because it is more likely that a data entry operator forgot to change the default value rather than the data entry operator actively selected the incorrect value. In the fields where m multiple modes exist, and the compared transcription contains one of the modes for that field, instead of counting the whole error, only (m−1)/m proportion of the error is counted.

Other factors can also be used to determine which mode (or modes) are considered to be the correct answer. For example, each mode has associated operators who have selected or data-entered that mode. The historical error rate of the associated operators may be used to determine which mode is correct. Other error rates may also be used, for example, the average error rate of the associated operators for the current field of interest, or averaged across the current set of documents.

Further, as the number of employees in each randomly selected group of employees increases, the probability of multiple modes for a given field correspondingly decreases. However, this decrease in probability may not necessarily be proportional to the increase in the number of employees. In one approach, once the plurality vote answer for each field in a document is identified, the plurality vote answers are combined, to automatically generate a plurality vote answer for the entire document.

The approaches used for multiple modes can also be applied to clusters. Clusters are the same as modes, except that the size of each cluster need not be the same highest number. Modes are the clusters with the largest (same) size. Other factors can also be used to estimate likelihood of error based on comparisons of answers, without knowing a priori which answer is the correct answer. For example, if different employees data-enter different answers for the same field, some of these answers may be consistent with previously identified error patterns. These answers may be assigned a higher likelihood of being in error.

The analysis of modes or clusters can also be used to learn equivalencies. So if clusters or modes of the phase "Lane" are highly correlated with clusters or modes of the phrase "Ln" then the software could learn that "Lane" is equivalent to "Ln" and thus this discrepancy should be ignored. This kind of learning can also be context specific such that St is considered equivalent to Street in certain contexts but not in others where St could be equivalent to Saint.

Each transcription entered by the employees is then electronically compared with its corresponding plurality vote answer. Any discrepancy between the two transcriptions is termed as an error, unless it has already been specified or learned. For example, if it is specified that 'Lane' may also be typed as 'Ln.', this discrepancy is not considered to be an error. By identifying the number of such errors, n is recorded for each field in the plurality of documents. The recorded values of n are then used to determine E. Accordingly, the value of E determined for a data entry operator is an absolute value, and is not relative to the error rates of other data entry operators.

As described above, various embodiments of the present invention eliminate the need for sampling documents with correctly known transcriptions. Such a process is completely automatic and can be carried out in a reliable manner wherein employees are not aware that they are being tested. This is because they have no way of differentiating the documents being used for sampling from the general flow of documents that they process. Therefore, an employee cannot 'game' the sampling.

As described earlier, w may be different for different fields. Further, an employee can make more errors in some fields of a document compared to other fields of the same document. Therefore, there can be critical fields in which the product of w and n are higher, compared to other fields. The expected operational risk can be controlled by either controlling n or reducing w in the critical fields. Reducing errors in the critical fields can control the n. Changing operating processes can control the w.

In an embodiment of the invention, critical fields within a document can be identified based on $e_i$. In an embodiment, a small set of fields from amongst the complete set of fields can be the critical fields. The employee/organization can substantially improve the overall quality, i.e., control the overall operational risk, by taking corrective/preventive actions in these critical fields. Since the corrective/preventive actions need to be taken in only a small set of fields, a greater proportion of expected operational risk can be avoided while incurring a proportionately lower cost.

Figure 3:
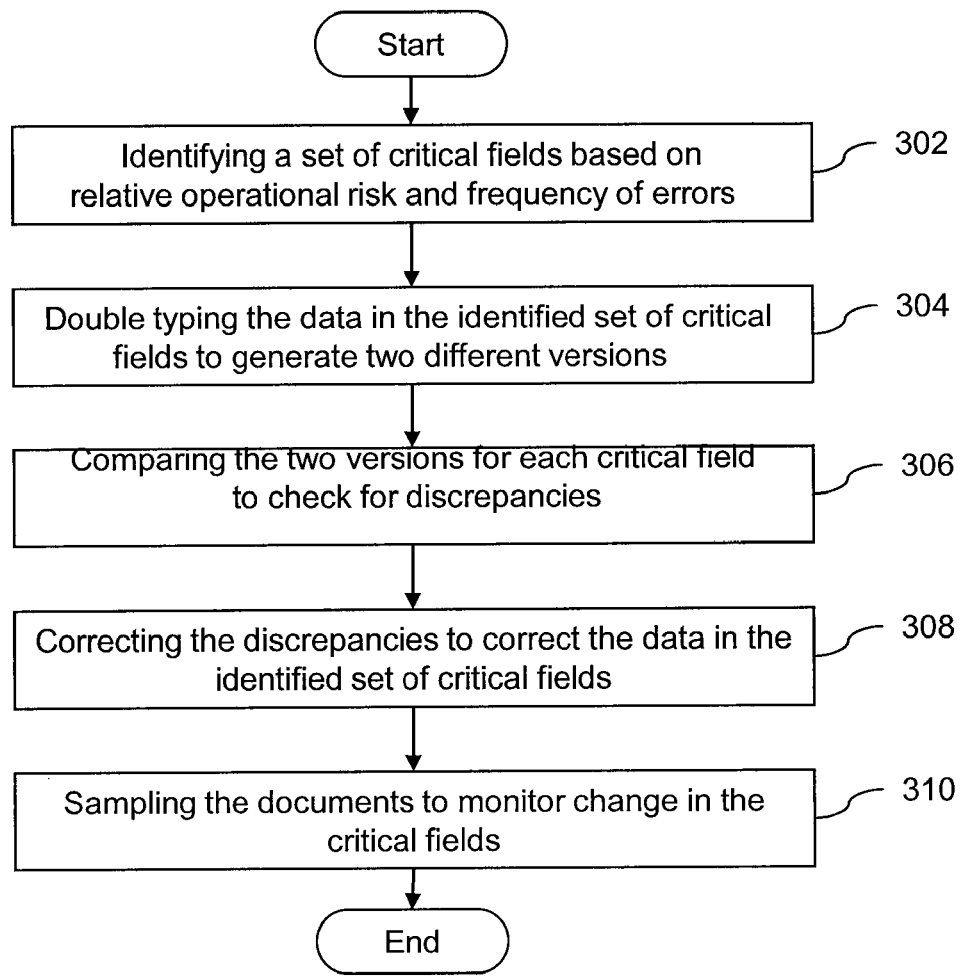
FIG. 3 is a flowchart depicting a method for reducing errors, in accordance with an embodiment of the present invention.

FIG. 3 is a flowchart of the system for reducing errors, in accordance with an embodiment of the present invention. At step 302, a set of critical fields is identified in the plurality of documents. The identification of this set is based on w and n. The error rate (e) of each field is determined, and the set of fields, of which the values of e are higher than a threshold, are identified as critical fields. For example, if 20% of the set of fields contribute 80% of the total error rate, then these 20% of the set of fields comprise the critical fields. In various embodiments of the invention, the identification of the critical fields can be automated.

In an embodiment of the present invention, the threshold is a predetermined value. In another embodiment of the present invention, the threshold depends on the operational impact and the value of n in each field in the plurality of documents. In another embodiment, the threshold is automatically set through standard applications such as 'goal seek' so that the sum of the e of the critical fields is equal to an arbitrary percentage (for example, 50%) of E (after accounting for any scaling factors).

The threshold is primarily set based on the customers' preference. Customers have to balance their risk tolerance and operational budget and decide their threshold for critical fields. The lower the risk appetite and the higher the operational budget, the greater is the percentage of document fields that can be considered critical fields. The distribution of errors among fields is also a factor determining the threshold. For example, if errors are highly concentrated among a few operationally important fields, then the threshold can be quite high (i.e. number of critical fields can be low) but still have the critical fields account for a significant proportion of expected operational risk.

The critical fields can also be similarly identified for each employee and training effort can be preferentially directed to the unique critical fields of each employee. This allows better targeting and customization and, therefore, better returns on investment of training activities.

At step 304, the data in the identified set of critical fields are double typed for each critical field. In other words, two different data entry operators type the data in each of the identified sets of critical fields. The typing generates two different versions of the data in each critical field. At step 306, the two versions are compared with each other, and any discrepancy between the two is termed as an error.

The errors are then removed at step 308, to correct the data in the identified set of critical fields. The errors can be removed through various ways. For example, a human supervisor may look into the error in order to mitigate it or the error may be removed by automatically calculating the plurality vote answer and then replacing the erroneous answer with the calculated plurality vote answer. As a result, errors in the critical fields can be substantially reduced. In an exemplary embodiment of the present invention, double typing 10% of the fields in the plurality of documents can reduce E by 50%. In this manner, double typing a small number of fields reduces E by a large factor. In other words, expending a small amount of labor and cost results in a large improvement in the quality of documents. Focusing on critical fields avoids undue usage of labor for error reduction. The documents with corrected data can be subsequently sampled again at step 310 to check the value of E. A decrease in E indicates a reduction in the operational risk. However, an increase or no change in E indicates that critical fields may have changed. Critical fields can change due to employee behavior or other changes in data entry operation. In such scenario, the critical fields can be automatically updated, i.e., new critical fields are identified and the steps 302-310 repeated again. The critical fields are also updated based on sampling. For example, companies may introduce process innovations that reduce error impacts or error frequency for the critical fields. As a result, the critical fields may shift. In such scenario, the critical fields are re-identified.

In an embodiment of the invention, once discrepancies are identified at step 306, the correct typing is manually identified. In another embodiment of the invention, rules based or artificial intelligence algorithms can be used to identify the correct typing.

In an embodiment of the present invention, identifying the 'root cause' of errors can help prevent errors. The root cause of errors may be determined by analyzing the error patterns in an automated or semi-automated manner. The error identification and measurement procedures provide rich data on error patterns. For example, the 'operational risk weighted error rate' for each employee for each data field can be easily identified. In some cases, a heavily skewed error pattern may be identified. In this case, for a given field, a small number of employees can have a disproportionately higher error rate than the average employees. This can indicate a training problem, which may be the root cause of these errors. In other cases, it may be found that almost all employees consistently make more errors in a particular field. This may indicate a process or system error.

Over a period of time, a database of such error patterns and their corresponding historical diagnosis can be generated. Subsequently, the database can be used to automatically predict fields that may have clearly identifiable root causes of errors. The database can additionally be used for diagnosing the possible cause of an error in that particular field. The database can be used to automatically predict the fields that may have clearly identifiable root causes of errors and what may be the possible diagnosis for that field. For example, the possible diagnosis may be a training, system, or process error. Further, the database can be used to indicate what were the historic diagnoses and corresponding solutions in the database for the error pattern in question. The prediction may be carried out using a simple correlation engine which identifies the most commonly occurring (or most highly correlated) root cause(s) for a given error pattern. Other techniques, such as more advanced clustering, pattern recognition and learning algorithms can be used to identify the appropriate cluster to which a specific error pattern belongs and what is the most likely diagnosis for that error pattern based on the database of previous error patterns and diagnoses.

Figure 4:
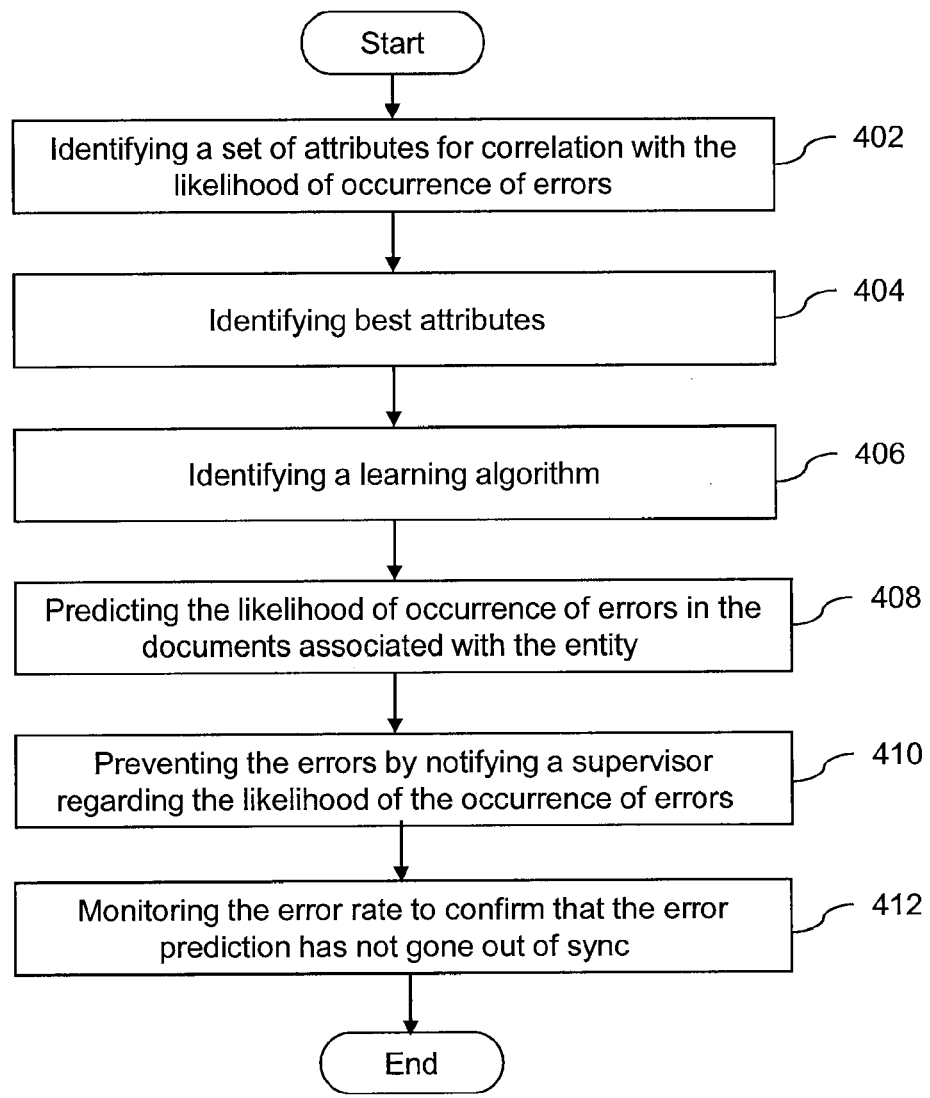
FIG. 4 is a flowchart depicting a method for preventing errors, in accordance with an embodiment of the present invention.

In an embodiment of the present invention, predicting the occurrence of errors can also prevent errors. FIG. 4 is a flowchart depicting the method for preventing errors by predicting the occurrence of errors (or by predicting an increase in the occurrence of errors). At step 402, a set of attributes is identified for correlation with the likelihood of occurrences of errors in the processed documents. At step 404, the attributes that are the best predictors of errors (most closely correlated with occurrences of errors) are identified. In various embodiments of the invention, a training process identifies the attributes. In an embodiment of the invention, the training is performed by using algorithms that measure correlation between an event (for example, an error) that has happened or not happened and an attribute (for example, the time of day). Other algorithms are based on artificial intelligence such as neural networks that use standard methodologies to identify such correlations.

In an embodiment of the present invention, data entry errors are mapped against various attributes to identify the best predictors of errors. For example, the occurrence of data entry errors can be mapped against the keystroke variability rate, i.e., the variation in the rate at which a user strokes the keys. It is observed that the frequency of errors increases with increase in the keystroke variability rate. Therefore, keystroke rate variability can be a good attribute for error prediction. Similarly, the occurrence of data entry errors is mapped against several other attributes to determine the attributes that are the best predictors of errors.

At step 406, an exemplary learning algorithm is selected to ensure best prediction of errors based on the identified attributes. Step 406 may alternatively be performed before step 404, i.e., a best predictive algorithm is first identified and then the algorithm is used in training mode to identify the best predictive attributes. At step 408, the correlation is determined between the errors in the plurality of documents and a set of attributes. This correlation is based on the identified learning algorithm. The learning algorithm can be based on for example, fuzzy logic, neural network, Bayes Nets, abstract local search and genetic algorithm.

A learning algorithm can establish a correlation between two events, for example, for two given events A and B. The learning algorithm can establish that if A occurs, it is likely that B also do so. Given a number of attributes, the learning algorithm can learn which attributes have the strongest correlation with, or are the best indicators of the occurrence of errors. Exemplary attributes can be the lighting conditions in the data entry operations, the complexity of the document being processed, the eye color of the data entry operator, the time when the errors were made, backlog levels when the errors occurred, and the variability of the keystroke rate of the data entry operator when the errors occurred.

Given these attributes, the learning algorithm can determine that the keystroke rate variability is a good indicator of the occurrence of errors. This correlation can now be used to predict the occurrence of errors. The learning algorithm can also determine that the eye color of the data entry operator is not correlated with him or her making errors. Therefore, the learning algorithm will reject this attribute.

Subsequently, at step 410, the supervisor is appropriately notified about the likelihood of errors occurring. For example, if the keystroke rate of a data entry operator shows high variations, a supervisor of the data entry operator can be notified that it is likely that the data entry operator may make an error in the near future. The supervisor can then take preventive actions to prevent errors. For example, the supervisor can verify the prediction by checking the data entered by the operator. Further, the supervisor can alert the data entry operator if errors are identified. The supervisor may also offer the data entry operator a short break or reduce his or her backlog levels. Alternatively, instead of notifying the supervisor, the system may initiate alternative preventative/corrective actions such as routing data for double typing. For example, the system can ask another employee to double type the data. It is to be noted these corrective and preventive actions are exemplary and any other corrective/preventive action can be taken without diverting from the scope and spirit of the invention.

At step 412, the error rate is monitored to confirm that the error prediction process has not gone out of synch. In an embodiment of the present invention, the plurality of documents is periodically sampled to monitor the error prediction process, and E is determined subsequently. Monitoring is required to check the correctness of the error prediction process, for example, the learning algorithm may predict that a particular operator is going to make errors. However, the next few documents typed by him may contain no errors. Such inconsistencies in error prediction can be verified, based on the value of E. For example, a low value of E in the above-mentioned case can imply that the learning algorithm has gone out of calibration. This is because the operator may adapt his behavior accordingly, for example, errors may occur when operators chat among themselves and stop typing while processing a document. In this case, each time an operator stops typing for more than fifteen seconds, the supervisor is notified that errors are likely to occur. The supervisor then checks on the operators. The operators may realize that the supervisor checks on them whenever they start chatting, and therefore stop chatting among themselves. This, in turn, can prevent the occurrence of errors due to chatting. However, errors may now occur due to other attributes not known to the learning algorithm. In such a situation, the learning algorithm is recalibrated. This recalibration may be initiated automatically or manually and can be achieved by updating the set of attributes, i.e., by identifying new attributes that are likely to cause errors and rejecting those that are not correlated to errors; and/or by selecting a better prediction algorithm as described in steps 404, and 406.

The error measurement algorithms described above, such as the plurality vote algorithm, generate rich data on the specific error patterns of each data entry employee. Such data can be used to double check the data entered by an employee. For example, an employee may have the habit of typing '7' instead of the character 'Z.' Such error patterns are highly employee-specific and generic rules to catch such errors may not be very effective. However, the employee-specific error patterns gathered through the error measurement algorithms can be used to customize deterministic algorithms specific to each employee (e.g., employee-specific rules), or to train learning algorithms specific to each employee. This specificity can significantly increase the effectiveness of such algorithms. This specificity can also be applied on a field by field basis, for example to generate field-specific rules or to train learning algorithms specific to each field.

The quality of the plurality of documents is managed in an embodiment of the present invention. E is measured to check the initial quality of the plurality of documents. The errors are then reduced, as described earlier. The occurrence of errors may also be prevented by identifying and mitigating 'root causes' of errors or by predicting such errors. The process of measuring E, and reducing errors can be performed repetitively to monitor and control the overall quality of the documents generated by the employee. It should be noted that the error measurement, reduction and prediction processes could operate independently. They can also operate simultaneously or at different times. These processes can make use of one or more sampling schemes, described earlier, to measure E. They can also use any other sampling scheme without limiting the scope of the present invention.

Figure 5:
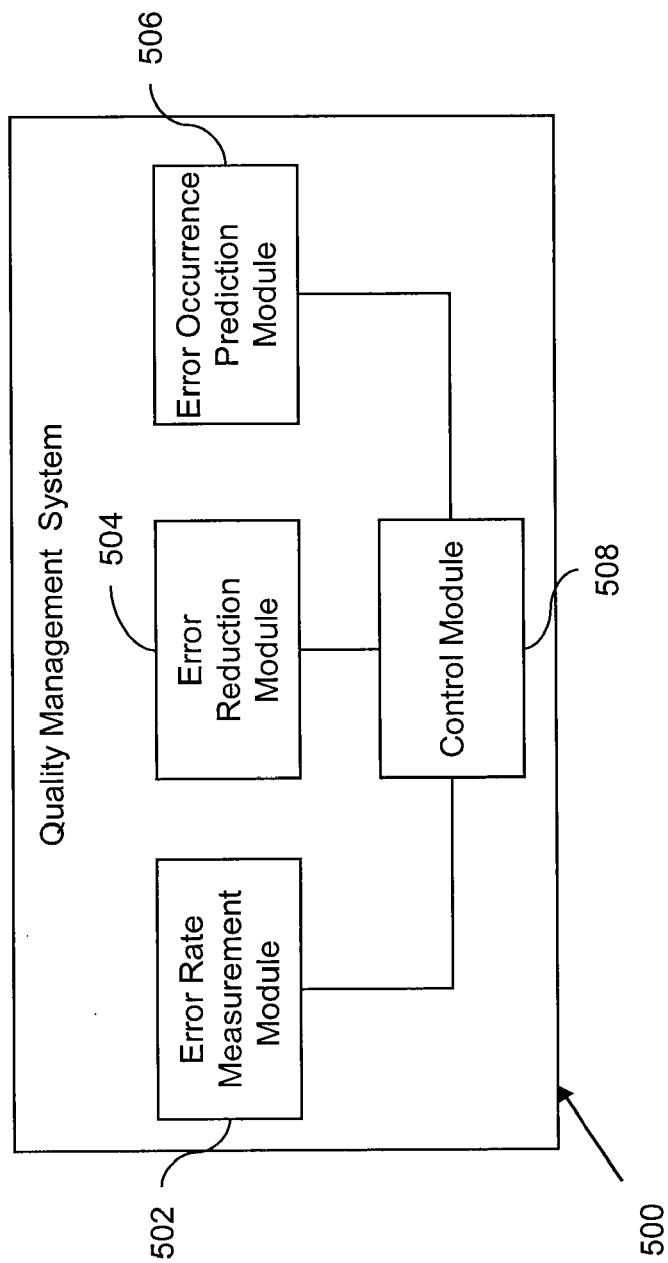
FIG. 5 is a block diagram illustrating a system for quality management, in accordance with an embodiment of the present invention.

The various embodiments of the method described above can be implemented by quality management system. In an embodiment of the present invention, this quality management system resides in quality management block 110. FIG. 5 is a block diagram illustrating quality management system 500, in accordance with an embodiment of the present invention. Quality management system 500 includes an error rate measurement module 502, an error reduction module 504, an error occurrence prediction module 506, and a control module 508. Error rate measurement module 502 is the means for determining E; error reduction module 504 enables reduction of the errors in the critical fields of the plurality of documents; and error occurrence prediction module 506 prevents errors by predicting their occurrence, and establishes a correlation between errors and a set of attributes by implementing learning algorithms. Control module 508 coordinates the other modules of the software system to control the quality of the plurality of documents. In particular, control module 508 monitors the change in the error rates on account of preventive/corrective actions taken to reduce the errors. Control module 508 updates the set of attributes for module 506 in case the attributes that impact the error occurrences change. Further, it periodically updates the critical fields for module 504. For example, companies may introduce process innovations that reduce error impacts or error frequency for the initially identified critical fields. Consequently, the critical fields can shift.

In various embodiments of the invention, system elements of quality management system 500 are implemented in the form of software modules, firmware modules and their combination thereof.

It is to be noted that while the various embodiments of the invention have been explained by using the example of data entry operation, the invention is applicable for any data processing operation such as data reporting, data storage and transformation. An exemplary data reporting operation can be an advance shipment note that is sent by a client to a recipient of the shipment as well as to the shipment agency, for example a courier agency. There can be discrepancies in the shipment notes send to the recipient and the shipment agency. The various embodiments of the invention can be used to measure the quality of reporting of shipment details by the client. Similarly, the error-identification technology or the plurality vote answer generation algorithm can be used to improve the error rate of Optical Character Recognition (OCR) systems. For example, the same document can be scanned by three or more different OCR systems, in order to automatically generate a plurality vote answer from the output of the OCRs. This plurality vote answer is likely to be more accurate than any of the individual OCR scans.

According to various embodiments of the invention, the error measurement algorithms, such as those based on the plurality vote answer generation algorithm, can also be used to quickly measure the operational risk due to differences in systems that are supposed to have identical output. For example, a bank may acquire another bank and wish to merge their existing systems. A random statistical sampling could be carried out with a representative sample, and the operational risk measure E could be used to quantify the discrepancies between the disparate systems that have to be consolidated. Similar experiments can be conducted at different points in infrastructure consolidation projects to quantify the reductions in discrepancy, and the improvements in consolidation achieved till date. Such approaches can be used to measure differences due to different organizations, due to different processes, due to different systems, or changes over time. For example, if a process is to be transferred from one organization to another, these approaches can be used to measure the differences between the original process and the transferred process, and to direct actions and/or to make changes to areas in the transferred process which would benefit the most. For example, the underlying patterns of the differences between the original process and the transferred process can be used to direct documentation efforts to the specific parts of the original process that seem to be ambiguous, direct potentially operator-specific training efforts to the parts of the transferred process that require the most training, and automation efforts to parts of the process that can be automated based on the patterns observed. These actions can be based on the measured errors, measured error rates (which accounts for both frequency of errors and relative operation risk) and/or error patterns (including patterns in the differences between the data-entered or the errors for the original and transferred processes).

The embodiments of the present invention have the advantage that they provide an error rate that directly measures the effectiveness in controlling the operational risk of an organization or employee corresponding to a data processing operation. The error rate can also be used to measure the expected operational risk of the data processing operation, thus it is useful for setting up accounting risk reserves and for meeting regulatory requirements (or other operational risk requirements) such as Sarbanes Oxley and Basel II.

The embodiments of the invention also allow rating/benchmarking of organizations and employees on the basis of how well they control operational risk, thus enabling an apples-to-apples comparison between organizations with different processes, document structure, size, etc.

The embodiments of the present invention offer a predominantly or completely automated method and system for reduction, prevention and prediction of errors in data processing operations. The various embodiments allow avoiding a large percentage of expected operational risk while expending a relatively small amount of labor. This is achieved by systematically focusing on the critical fields of the document, which accounts for a disproportionately high percentage of the total expected risk. Further, the identification of the critical fields is automated.

Various embodiments of the present invention eliminate the need for sampling documents with known correct transcriptions. Such a process is completely automatic and can be reliably carried out in a manner where employees are not aware that they are being tested. This is because they have no way of differentiating the documents being used for sampling from the general flow of documents that they process. Therefore, an employee cannot 'game' the sampling.

Other embodiments of the invention provide a method for identifying critical fields for each employee. Therefore, training effort can be directed toward the critical fields identified for each employee. This allows tailored targeting/customization, thereby ensuring better returns on investment of training activities. Error rates can also be estimated without identifying which specific operator was responsible for a discrepancy. Error rate estimation can be achieved by sampling a small number of documents.

Further, since the process is automated, the quality management can be performed real time. Further, the employees need not be aware that their quality is being audited. Further, unlike in training intensive procedures such as "Six Sigma" the data entry operators do not need to be specifically trained to use these methodologies which may be automated.

In certain aspects described above, the same or similar set of documents is given to multiple operators for processing. This is because we analyze the differences in the ways in which each operator processes the same document, determine the normative behavior based on the methods described above, identify deviations from that norm, and then optionally find underlying patterns to those deviations from the norm. It should be noted that the sets of similar documents can be generated in various ways. For example, one document could be duplicated multiple times, thus producing multiple versions of the same document. Alternately, documents that are sufficiently similar may already exist. In that case, those documents need only be identified as being similar. The identification can be done before or after processing by the operators.

For example, we can look at treatment decisions of doctors when faced with similar patients. In this example, rather than taking a single patient case and duplicating it for many doctors, we identify different patients whose cases are similar enough for the analysis at hand. For purposes of the analysis, there are naturally occurring "duplicates." Let's say the vast majority of doctors prescribe a set of medicines within an acceptable level of difference in prescription details. However, some of them instead recommend surgery. This can be identified as a deviation from the norm.

The plurality vote and cluster analysis techniques described earlier can be applied here. The concepts of specified equivalencies (such as a table of equivalent medications) or learned equivalencies can be applied while determining the norm. Optionally we can look at a database of previously observed deviation patterns and predict whether a specific behavior is a benign variance or a significant error. Historic patterns of behavior for operators (same as "historic error rates") can be further used for cases where there are multiple significantly sized clusters, to identify the true normative behavior. Classes of activities could be analogized to fields, and we could then apply the techniques used to consider different fields and the relative operational risk from errors in a given field. Similarly, a set of classes of activities that can be treated as a unit could be analogized to a document. Thus, each of the medical steps from a patient's initial visit to a doctor, to a final cure may be treated as a document or transaction. So, for example, pre-treatment interview notes, initial prescription, surgery notes, surgical intervention results, details of post-surgery stay, etc. would each be treated as a "field" and would have related weights of errors. The overall error E would be the weighted average of the errors in the various fields. As in the previously described methods, the occurrence of errors can be correlated to a set of process and external attributes to predict future errors. A database of error patterns and the corresponding historical root causes can also be generated and this can be used to diagnose the possible cause of an error in a field/class of activity. Continuing the analogy, the data on the error patterns of each operator, here a doctor or a medical team, can be used to create operator and/or field specific rules to reduce or prevent errors.

In another example, we can look at financial decisions of people with similar demographics and other characteristics. Let's say the vast majority of them buy a certain amount of stocks and bonds within an acceptable level of difference in portfolio details. However, some of them instead buy a red convertible. This might be a deviation from a norm and could be analyzed similarly.

Alternatively, it may not be necessary to find documents which are similar in all ways. A search can be conducted for segments of the data which share as few as one or more similar field or parameter values. For example, a database of loan applications can be searched for applicants between 37 and 39 years of age. Any pair of applications from this sample might be no more similar than a randomly chosen pair from the population. However, this set of applications can be statistically analyzed to determine whether certain loan officers are more likely to approve loans from this section of the population.

Furthermore, it may not be necessary to find even one very similar parameter. Large segments of the population may be aggregated for analysis using criteria such as "applicants under 32 years old" or "applicants earning more than $30,000 per year." Extending this methodology one step further, a single analysis can be conducted on the sample consisting of the entire population.

In addition, it is possible to analyze sets of data which do not contain all of the information that the operators use to make decisions. In the case of loan applications requiring a personal interview, it would be very hard to conduct a controlled experiment that includes the personal interview. It would also be difficult to search for "similar" interviews. However, we can still search for applications with some parameters similar, and aggregate the statistics across all interviews. It may not be possible to identify any single loan decision as incorrect or suspect, but if, for example, among applicants aged 26-28, earning over $32,000, one loan officer approves 12% of loans and another approves 74% of loans, there may be training or other issues.

These methods can be combined to find a diverse variety of samples to analyze. A sample might consist of the documents with each field similar to a given value for that field, or it might comprise the set of all the documents. In addition, some fields may be restricted to a small or large range, where other fields have no restriction. Each sample may be analyzed with statistical methods to determine whether operators are processing documents consistently.

There are several statistical hypothesis tests which may be appropriate for making this determination. If the output of the process is binary, such as a loan approval, and the number of documents in the sample under analysis is small, a test such as Fisher's Exact Test may be used. If the output is a number, such as a loan interest rate, and the sample is large, a Chi-Square Test may be used. These tests can be used to determine whether one operator is producing significantly differing output from the remainder of the operators. Alternately, the operators can be split into two groups and these tests can be used to determine whether the operators in the two groups are producing significantly differing output. All possible splits can be analyzed to find the one with the highest statistical significance. Alternately, these tests can be used to determine simply whether the distribution of operator output for this sample is significantly more unusual than what would be expected under the null hypothesis, i.e., all operators making decisions in the same manner.

If numerous statistical tests are conducted, it is expected that some of them will be statistically significant, even without any underlying pattern. It is important to search for p-values which are more extreme than would normally be sought. For example, if 1000 tests are conducted, we could require a p-value of 0.00005 rather than the typical 0.05. Alternately, we can split the data into two sets of data: a training set and a testing set. We can conduct a large number of tests on the training data, but may find that our lowest p-values are not statistically significant due to the large number of tests conducted. We can then use the results to construct new hypotheses and design a small number of new tests. These new tests can be conducted on the testing data set. Because only a few tests are being conducted, we would not need very extreme p-values to achieve significance. Alternately, we can use the results as a starting point for any other review process, including supervisor review of indicated historic documents. Rules can potentially also be created to automatically flag documents from this segment of the population, as they are processed, for additional review.

Another method for computing the statistical significance of complicated test statistics is as follows. We are testing against the null hypothesis that all operators behave in the same manner. Disproving this null hypothesis means there is some statistically significant underlying pattern to the behavior of the operators. For statistics where operators are separated into multiple groups under a grouping plan, we can randomly assign operators into groups repeatedly under multiple different grouping plans and re-compute the test statistic for each grouping plan. If the value for a specific grouping plan is higher than the value for 95% of randomized grouping plans then we have 95% confidence that our null hypothesis was incorrect. Of course, we cannot simply compute many random grouping plans and assert that the top few grouping plans are statistically significant. However, we can identify a possibly significant grouping plan by doing this for the training dataset, and see if that grouping plan is again in the best 5% of random grouping plans for the testing data set.

It should be noted that a statistical hypothesis test can be very useful for showing that one or more operators produce different output (or a different output distribution) for documents from the same section of the population. However, it may be more valuable to find sections of the population where the operator output difference is large, rather than merely statistically significant. Metrics other than statistical p-value can be used to determine which population sections require further study. One such metric is related to the variance in the means of the operators output. Because we only have access to a sample of the data, we typically cannot compute the actual means. We can instead compute an estimate of each of the means and use this to calculate an estimate of the variance in the means.

In a stable process where there were no deviations from the norm, the variance would be significantly lower than in a process with patterns of deviations from the norm. Any of these metrics, or others, can be used as the basis of a hill climb or other local search method to identify interesting samples of the population that would be most useful to analyze to detect underlying patterns of deviations from norms or fragmented norms. A key property of these metrics is that they are highest for the section of the document population that actually represents the variance in operator behavior. For example, if one operator is not approving loans from males aged 20-30, the metric should be higher for "males aged 20-30" than for "males aged 20-50" and "people aged 20-30."

Local search methods operate by considering a given sample, and repeatedly modifying it with the goal of raising the metric. This continues until the metric is higher for the sample under consideration than for any nearby samples (a local optimum). The notion of proximity is complex for samples of the sort we are discussing. The "modify" step in the algorithm will change the restrictions defining the current sample. This can consist of widening or tightening the restriction on one field, or adding a restriction on a new field, or removing the restriction on a restricted field. For example, if we consider a sample consisting of "Loan applications from females aged 30-40" and calculate the metric to be X, we could then calculate the metric for "females", "females aged 30-50", "females aged 20-40", "people aged 30-40", and others. Each of these metrics will be compared to X and the search algorithm will continue.

Because the metrics are highest for samples with acute variances, very small samples will have low values for the metric, as will very large ones. As the search algorithm runs, the sample under consideration will "evolve" to contain the features that are causing the discrepancy in operator processing while not containing unrelated random information. Of course, the search will cease on one local maximum. If the local search is repeated multiple times from random starting samples, many samples with peak metrics can be identified in the data.

It is also possible to identify situations where transactions could be automatically processed. If the vast majority of the documents with certain properties are processed with the same "certain output", then future documents satisfying those properties could be automatically processed without requiring human effort. For example, if it turns out that 99.99% of loans where the loan amount was less than the applicant's six months' salary were approved, then such loans may be automatically processed. If other outputs occur less frequently than the error rate for this process, then simply mechanically applying this "certain output" instead of allowing operators to process the document will actually be more accurate.

The decision can be made by calculating our best estimate of the portion of documents with these properties that have the certain output. To do this we can calculate a "posterior probability" for the suspected output using the documents in the sample having these certain properties. The posterior probability is the conditional probability that is assigned after the relevant evidence is taken into account. In order to make this estimate, we need to know two things: the a priori probability that a generic category of documents will have this certain output, and the portion of documents in this sample that have this certain output. It is difficult to know the exact prior probability distribution, so we can assume a reasonable approximation, for example, the uniform distribution from 0 to 1. If M documents out of N in the sample have outputs other than the "certain output," then the probability of an additional sample with these properties having this output can be computed from the Beta Distribution to be equal to $(N+1)/(N+M+2)$.

Such analysis identifies patterns of automated decisioning that may not be obvious to the process owners. Complex supply chains can be analyzed in similar ways. For example, a retailer may wish to analyze its supply chain to figure out underlying patterns of product damage or pilfering or delayed shipments. This method could even be applied to automated systems such as electrical smart grids and complex computer networks to determine root causes of errors.

The pattern of error E for a given operator over time can be used for additional analysis. Traditional correlation analysis predicts an outcome based on the current value of a variable based on correlation formulas learnt based on other observations. If the current value of the variable is 10, traditional correlation analysis will predict the same outcome regardless of whether the variable hit the value 10 at the end of a linear, exponential, sine, or other function over time. However, E can be measured for operators over time and the pattern of E over time (whether it was linear, exponential, random, sinusoidal, etc.) can be used to predict the future value of E. Moreover, one can observe how E changes over time and use learning algorithms to identify process and external attributes that are predictors of the pattern of changes in E over time. These attributes can then be used to predict the pattern of the future trajectory of the error E for other operators or the same operator at different points in time. Such an analysis would be a much more accurate predictor of future outcomes than traditional methods like simple correlation analysis.

One may also observe E for a set of operators with similar characteristics over time. In some cases, E of all of the operators in the set will shift similarly and this would be an evolution in the norm. However, in some cases, E for some of the operators will deviate from E for the other operators and form a new stable norm. This is a split of the norm. In the other cases, E for multiple distinct sets of operators will converge over time and this is a convergence of norms. Finally the errors E for a small subset of operators may deviate from E for the rest of the operators but not form a new cohesive norm. This would be a deviation of the norm. Learning algorithms may be used to find process and external attributes that are best predictors of whether a set of operators will exhibit a split, a convergence, an evolution or a deviation of the norm. Similar learning algorithms may be used to predict which specific operators in a given set are most likely to exhibit a deviation from the norm. Other learning algorithms may be used to predict which specific operators in a given set are most likely to lead an evolution or splitting or convergence of a norm. By observing E for such lead operators, we can better predict the future E for the other operators in the same set.

As described above, the error E here can be for data entry, data processing, data storage and other similar operations. However, it can also be for healthcare fraud, suboptimal financial decision-making, pilferage in a supply chain, or other cases of deviations from the norm or from an optimal solution.

The system, as described in the present invention or any of its components, may be embodied in the form of a computer system. Typical examples of a computer system include a general-purpose computer, a programmed microprocessor, a micro-controller, a peripheral integrated circuit element, and other devices or arrangements of devices that are capable of implementing the steps that constitute the method of the present invention.

The computer system comprises a computer, an input device, a display unit and the Internet. The computer comprises a microprocessor. The microprocessor can be one or more general- or special-purpose processors such as a Pentium®, Centrino®, Power PC®, and a digital signal processor. The microprocessor is connected to a communication bus. The computer also includes a memory, which may include Random Access Memory (RAM) and Read Only Memory (ROM). The computer system also comprises a storage device, which can be a hard disk drive or a removable storage device such as a floppy disk drive, optical disk drive, and so forth. The storage device can also be other similar means for loading computer programs or other instructions into the computer system. The computer system also includes one or more user input devices such as a mouse and a keyboard, and one or more output devices such as a display unit and speakers.

The computer system includes an operating system (OS), such as Windows, Windows CE, Mac, Linux, Unix, a cellular phone OS, or a proprietary OS.

The computer system executes a set of instructions that are stored in one or more storage elements, to process input data. The storage elements may also hold data or other information as desired. A storage element may be an information source or physical memory element present in the processing machine.

The set of instructions may include various commands that instruct the processing machine to perform specific tasks such as the steps that constitute the method of the present invention. The set of instructions may be in the form of a software program. The software may be in various forms, such as system software or application software. Further, the software may be in the form of a collection of separate programs, a program module with a larger program, or a portion of a program module. The software might also include modular programming in the form of object-oriented programming and may use any suitable language such as C, C++ and Java. The processing of input data by the processing machine may be in response to user commands to results of previous processing, or in response to a request made by another processing machine.

While the preferred embodiments of the invention have been illustrated and described, it will be clear that it is not limited to these embodiments only. Numerous modifications, changes, variations, substitutions and equivalents will be apparent to those skilled in the art, without departing from the spirit and scope of the invention, as described in the claims.

What is claimed is:

1. A computer-implemented method for analyzing a behavior of different entities performing similar tasks, the method comprising:
    observing outputs of multiple similar tasks with similar inputs performed by different entities;
    identifying clusters of outputs based on similarities and dissimilarities between outputs; and
    determining a normative behavior for the entities based on a size of the clusters, wherein larger size clusters define the normative behavior.

2. The method of claim 1 further comprising:
    identifying possible abnormal behavior, based on smaller size clusters that deviate from the normative behavior.

3. The method of claim 1 further comprising:
    identifying a split in normative behavior, based on a large cluster evolving over time into two large clusters.

4. The method of claim 1 further comprising:
    identifying a merge in normative behavior, based on two large clusters evolving over time into a single large cluster.

5. The method of claim 1 further comprising:
    identifying an evolution in normative behavior, based on a large cluster evolving over time into a single large cluster characterized by different behavior.

6. The method of claim 1 wherein the entities performing tasks are doctors treating patients.

7. The method of claim 1 wherein the entities performing tasks are operators processing documents.

8. The method of claim 1 wherein the entities performing tasks are entities making financial decisions.

9. The method of claim 1 wherein the entities performing tasks are entities performing activities as part of a supply chain.

10. The method of claim 1 wherein the entities performing tasks are hospitals treating patients.

11. The method of claim 1 wherein the entities performing tasks are organizations issuing bills for goods and services rendered.

12. The method of claim 1 wherein the entities performing tasks include adverse event reports issued corresponding to a medicine or medical procedure or medical device.

13. The method of claim 1 wherein the entities performing tasks are monitoring reports on an electricity smart grid.

14. A computer program product for analyzing a behavior of different entities performing similar tasks, the computer program product stored on a tangible computer-readable medium and including instructions that, when loaded into memory, cause a processor to carry out the steps of:
    observing outputs of multiple similar tasks with similar inputs performed by different entities;
    identifying clusters of outputs based on similarities and dissimilarities between outputs; and
    determining a normative behavior for the entities based on a size of the clusters, wherein larger size clusters define the normative behavior.

15. The computer program product of claim 14 wherein the computer program product causes the processor to carry out the further step of:
    identifying possible abnormal behavior, based on smaller size clusters that deviate from the normative behavior.

16. The computer program product of claim 14 wherein the computer program product causes the processor to carry out the further step of:
    identifying a split in normative behavior, based on a large cluster evolving over time into two large clusters.

17. The computer program product of claim 14 wherein the computer program product causes the processor to carry out the further step of:
    identifying a merge in normative behavior, based on two large clusters evolving over time into a single large cluster.

18. The computer program product of claim 14 wherein the computer program product causes the processor to carry out the further step of:
    identifying an evolution in normative behavior, based on a large cluster evolving over time into a single large cluster characterized by different behavior.

19. A computer-implemented method for analyzing a behavior of different entities, the method comprising:
    identifying multiple similar tasks with similar inputs performed by different entities;
    identifying clusters of outputs based on similarities and dissimilarities between outputs; and
    determining a normative behavior for the entities based on a size of the clusters, wherein larger size clusters define the normative behavior.

* * * * *

UNITED STATES PATENT AND TRADEMARK OFFICE
CERTIFICATE OF CORRECTION

PATENT NO. : 8,782,087 B2
APPLICATION NO. : 13/249168
DATED : July 15, 2014
INVENTOR(S) : Arijit Sengupta, Brad A. Stronger and Daniel Kane Page 1 of 1

It is certified that error appears in the above-identified patent and that said Letters Patent is hereby corrected as shown below:

Title Page, Item (63) Related U.S. Application Data, lines 9-10, delete ", which is a continuation-in-part of application No. PCT/US2011/037956," and replace with --. Also a continuation-in-part of application No. PCT/US2011/037956,--.

Signed and Sealed this
Sixteenth Day of June, 2015

Michelle K. Lee
*Director of the United States Patent and Trademark Office*